(12) United States Patent
Bassler et al.

(10) Patent No.: US 7,500,987 B2
(45) Date of Patent: Mar. 10, 2009

(54) AMORPHOUS ALLOY STENTS

(75) Inventors: Brad Bassler, Tampa, FL (US);
Tranquoc Thebao Nguyen, Anaheim, CA (US); Atakan Peker, Aliso Viejo, CA (US); David Opie, Annapolis, MD (US)

(73) Assignee: Liquidmetal Technologies, Inc., Rancho Santa Margarita, CA (US)

( * ) Notice: Subject to any disclaimer, the term of this patent is extended or adjusted under 35 U.S.C. 154(b) by 353 days.

(21) Appl. No.: 10/534,374

(22) PCT Filed: Nov. 18, 2003

(86) PCT No.: PCT/US03/36934
§ 371 (c)(1),
(2), (4) Date: Oct. 4, 2005

(87) PCT Pub. No.: WO2004/045454
PCT Pub. Date: Jun. 3, 2004

(65) Prior Publication Data
US 2006/0122687 A1 Jun. 8, 2006

(51) Int. Cl.
*A61F 2/06* (2006.01)
*C22C 45/10* (2006.01)

(52) U.S. Cl. ..................... 623/1.15; 148/561

(58) Field of Classification Search ....... 623/1.11–1.15, 623/23.55; 148/421, 561
See application file for complete search history.

(56) References Cited

U.S. PATENT DOCUMENTS

| | | | |
|---|---|---|---|
| 3,989,517 A | 11/1976 | Tanner et al. | |
| 4,050,931 A | 9/1977 | Tanner et al. | |
| 4,064,757 A | 12/1977 | Hasegawa | |
| 4,067,732 A | 1/1978 | Ray | |
| 4,113,478 A | 9/1978 | Tanner et al. | |
| 4,116,682 A | 9/1978 | Polk et al. | |
| 4,116,687 A | 9/1978 | Hasegawa | |
| 4,126,449 A | 11/1978 | Tanner et al. | |
| 4,135,924 A | 1/1979 | Tanner et al. | |
| 4,148,669 A | 4/1979 | Tanner et al. | |
| 4,623,387 A | 11/1986 | Masumoto et al. | |
| 4,648,609 A | 3/1987 | Deike | |
| 4,721,154 A | 1/1988 | Christ et al. | |
| 4,743,513 A | 5/1988 | Scruggs | |
| 4,976,417 A | 12/1990 | Smith | |
| 4,987,033 A | 1/1991 | Abkowitz et al. | |
| 4,990,198 A | 2/1991 | Masumoto et al. | |
| 5,032,196 A | 7/1991 | Masumoto et al. | |
| 5,053,084 A | 10/1991 | Masumoto et al. | |
| 5,053,085 A | 10/1991 | Masumoto et al. | |
| 5,213,148 A | 5/1993 | Masumoto et al. | |
| 5,250,124 A | 10/1993 | Yamaguchi et al. | |
| 5,279,349 A | 1/1994 | Horimura | |
| 5,288,344 A | 2/1994 | Peker et al. | |
| 5,368,659 A | 11/1994 | Peker et al. | |
| 5,380,375 A | 1/1995 | Hashimoto et al. | |
| 5,384,203 A | 1/1995 | Apfel | |
| 5,449,425 A | 9/1995 | Renard et al. | |
| 5,482,580 A | 1/1996 | Scruggs et al. | |
| 5,567,251 A | 10/1996 | Peker et al. | |
| 5,711,363 A | 1/1998 | Scruggs et al. | |
| 5,797,443 A | 8/1998 | Lin et al. | |
| 5,886,254 A | 3/1999 | Chi | |
| 5,950,704 A | 9/1999 | Johnson et al. | |
| 6,021,840 A | 2/2000 | Colvin | |
| 6,027,586 A | 2/2000 | Masumoto et al. | |
| 6,044,893 A | 4/2000 | Taniguchi et al. | |
| 6,200,685 B1 | 3/2001 | Davidson | |
| 6,258,183 B1 | 7/2001 | Onuki et al. | |
| 6,306,228 B1 | 10/2001 | Inoue et al. | |
| 6,371,195 B1 | 4/2002 | Onuki et al. | |
| 6,376,091 B1 | 4/2002 | Croopnick | |
| 6,408,734 B1 | 6/2002 | Cohen | |
| 6,446,558 B1 | 9/2002 | Peker et al. | |
| 6,767,418 B1 * | 7/2004 | Zhang et al. ................. | 148/421 |
| 2001/0052406 A1 | 12/2001 | Kubota et al. | |
| 2002/0036034 A1 | 3/2002 | Xing et al. | |
| 2002/0050310 A1 | 5/2002 | Kundig et al. | |
| 2006/0108033 A1 * | 5/2006 | Peker et al. .................. | 148/561 |
| 2006/0149391 A1 * | 7/2006 | Opie et al. ............... | 623/23.55 |

FOREIGN PATENT DOCUMENTS

| | | |
|---|---|---|
| JP | 06-264200 | 9/1994 |
| JP | 2000-256811 | 9/2000 |

OTHER PUBLICATIONS

Zhang et al., "Amoprphous Zr—Al—TM (TM=Co, Ni, Cu) Alloys with Significant Supercooled Liquid Region of Over 100K", Materials Transactions, JIM., 1991, vol. 32, No. 11, pp. 1005-1010.
Inoue et al., "Zr—Al—Ni Amorphous Alloys with High Glass Transition Temperature and Significant Supercooled Liquid Region", Materials Transactions, JIM, 1990, vol. 31, No. 3, pp. 177-183.
Tanner et al., "Physical Properties of $Ti_{50}Be_{40}Zr_{10}$ Glass", Sripta Metallurgica, Jun. 22, 1977, vol. 11, pp. 783-789.
Tanner, L.E., "Physical Properties of Ti—Be—Si Glass Ribbons", Scripta Metallurgica, 1978, vol. 12, pp. 703-708.
Hasegawa et al., "Superconducting Properties of Be—Zr Glassy Alloys Obtained by Liquid Quenching", May 9, 1977, pp. 3925-3928.
Tanner, L.E., "The Stable and Metastable Phase Relations in the Hf—Be Alloy System", Metallurgica, vol. 28, 1980, pp. 1805-1815.
Maret et al., "Structural Study of $Be_{43}Hf_xZr_{57-x}$ Metallic Glasses by X-Ray and Neutron Diffraction", J. Physiq, 1986, vol. 47, pp. 863-871.
Jost et al., "The Structure of Amorphous Be—Ti—Zr Alloys", Zeitschrift fur Physikalische Chemie Neue Folge, Bd. 157, 1988, pp. 11-15.
Tanner et al., "Metallic Glass Formation and Properties in Zr and Ti Alloyed with Be—I The Binary Zr—Be and Ti—Be Systems", Acta Metallurgica, 1979, vol. 27, pp. 1727-1747.

* cited by examiner

*Primary Examiner*—Suzette J Gherbi
(74) *Attorney, Agent, or Firm*—Kauth, Pomeroy, Peck & Bailey LLP

(57) ABSTRACT

Stents made of bulk-solidifying amorphous alloys and methods of making such stents are provided.

30 Claims, 3 Drawing Sheets

AMORPHOUS ALLOY STENTS

FIELD OF THE INVENTION

The present invention relates to stents made of bulk-solidifying amorphous alloys and methods of making such articles.

BACKGROUND OF THE INVENTION

Stents are small and expandable tubulur members, which are inserted into clogged blood vessels to restore proper blood flow, or to treat other damaged passageways or lumens in the body, like bronchi or the esophagus. In turn, placing a stent implant (stenting) is often a catheter-based procedure. In the example of vascular stenting, a catheter is used to place a stent into a diseased artery to maintain the vessel patency after balloon angioplasty. In another application, covered stents (called stent-grafts) are also used to treat aneurysms, including abdominal aortic aneurysms. In a stent-graft procedure, the physician prevents blood from filling the aneurysm (bulge in artery) by placing a stent graft at the aneurismal site.

Generally there are two classes of stents: balloon-expanded stents, and self-expanding stents. Balloon expanded stents are initially small enough to enter the body lumen easily and are fitted over a collapsed balloon. The stent is then expanded through plastic deformation as the balloon is inflated. After inflation, the stent is in tight approximation to the lumen wall. The specific design of the stent struts (mesh segments) is optimized to provide a flexible, unexpanded structure that can track through the body cavities during insertion, and a patent lumen after expansion. Self-expanding stents are naturally sized for tight fit in the target lumen, but held in a compressed state during delivery through the body lumens to the target site. Once the self-expanding stent is located at the target lumen site, then the stent is release and allowed to spring back to its natural, expanded size. Design considerations similar to those followed with balloon-expanded stents are used in the design of a self-expanding stent. The self-expanding stent must track through the vasculature in the collapsed state and fit the lumen when expanded to provide patency. The struts of the self-expanding are designed to elastically deform during compression and return to a predetermined final shape. Those can be made of a wire-mesh or a specially designed pattern of slots or apertures.

Specific stent strut structures include wire-mesh, specially designed pattern of slots or apertures, coiled springs, helical wound spring coil, expanding forms in a zig-zag pattern, diamond shaped, rectangular shaped, and other mesh and non-mesh designs. Stents come in different sizes and designs depending on the many factors. Some of the factors include: 1) the size of the artery in consideration; 2) where the blockage is located; 3) the extent of the blockage; 4) the extent of blockage in other arteries; 5) the strength of the heart muscle; and 6) the interaction of the implanted stent with the vascular (or target lumen) physiology.

Despite the number of different considerations used in the designing a stent, the variety of materials used is quite limited. For example, stainless steel is the most common metal used for stents although, nitinol is also gaining wide-spread acceptance.

The quality of stent's function can be measured in terms of acute performance and chronic performance. Acutely, the stent keeps the lumen wall from recoiling after balloon expansion, and keeps dissected flaps from causing acute closure at the angioplasty site. Chronic performance of a stent is gauged by the degree of restenosis (re-blockage) in the treated lumen. Restenosis is considered to be a proliferative cellular response to the injury caused during angioplasty and stent implantation. Approximately 20 percent of stents close (restenose) within six months of placement.

Improving stent performance can be measured against several other criteria: 1) designing smaller diameter stents (less than 2.5 millimeters) for smaller vessels; 2) custom-designing stents for an optimal fit; 3) designing stents for multiple sites within the same artery (including stents with side branches); and 4) providing effective coating of stents with anticoagulants and antiproliferation agents.

Unfortunately, current materials used in stents are not readily adaptable to many of these desired improvements. The limitations of the current stent materials include both limited fabricability, and non-optimal physical and mechanical properties. For example, the mechanical properties of stainless steel and nitinol depend on the history of thermomechanical process history. As such, various fabrication and finishing steps can result in inconsistent or inferior physical and mechanical properties. Furthermore, the physical and mechanical properties of current materials are not generally sufficient for the development of new novel stent designs, such as stents having diameters less than 2.5 mm.

Accordingly, a need exists for a new class of materials to address the material and fabrication deficiencies of current materials as well as to provide options and tailorable properties for the various demands of stents.

SUMMARY OF THE INVENTION

The current invention is directed to stents made of bulk-solidifying amorphous alloys and methods of making such stents.

In one embodiment of the invention, the stent is made of a bulk-solidifying amorphous alloy. In one preferred embodiment of the invention, the stent is made of Zr/Ti base bulk-solidifying amorphous alloy.

In another embodiment of the invention, the stent has a hexagonal or round cross-section.

In still another embodiment of the invention, the stent is a coiled spring, helical wound spring coil, zig-zag pattern, diamond shaped, and other mesh and non-mesh designs.

In yet another embodiment of the invention, the wall of the stent has multiple aperture openings.

In still yet another embodiment of the invention, the stent is braided to improve flexibility in longitudinal direction and strength in radial direction.

In still yet another embodiment of the invention, the percentage of vessel covered by the stent is between 9 to 20%.

In still yet another embodiment of the invention, the percentage of vessel covered by the stent is more than 80%.

In still yet another embodiment of the invention, the stent is porous in the form of wire, tube or metal sheet, used for treating vasculature disease by delivering medication to the implant site.

In still yet another embodiment of the invention, the bulk solidifying amorphous alloy component of the stent is coated with anticoagulants (preventing the formation of a blood clot in the stent) and/or chemotherapeutic drugs to potentially minimize restenosis.

In still yet another embodiment of the invention, the stent contains at least one drug is loaded into the pores.

In still yet another embodiment of the invention, the cover tubes is porous and contains medicine or other substances to improve the performance of the stent.

In still yet another embodiment of the invention, the stent is a covered stent in which the stent is covered with a tube or multiple tubes made of metal, biodegradable material, plastic or other material.

In still yet another embodiment of the invention, the stent is a covered stent in which the stent is covered with a tube or multiple tubes made of metal, biodegradable material, plastic or other material and which are impregnated with an anticoagulant and/or chemotherapeutic drugs to potentially minimize restenosis.

In still yet another embodiment of the invention, the stents are coated with radioactive material, or other bioactive substances to improve the performance of the stent.

In still yet another embodiment of the invention, the stent is made up of two or more tubular stent segments which may be deployed together so to produce a single axial length by a provision of overlapping or abutting areas. In such an embodiment the cross section of the stent may vary according to the blood vessel.

In still yet another embodiment of the invention, the stent is to be self-expanding and therefore does not need a separate angioplasty balloon for its expansion.

In still yet another embodiment of the invention, the stent has branches that support multiple vessels at a bifurcation.

In still yet another embodiment of the invention, the wall thickness of the stent is less than 0.5 mm, and preferably less than 0.25 mm.

In still yet another embodiment of the invention, the stent covering has different porosities in different regions. In those regions, typically the ends, where tissue ingrowth and re-endothelialization are desired, the stent covering is more porous, and in those regions were it is desirable to inhibit such in growth, the stent covering is substantially non-porous.

In still yet another embodiment of the invention, the pore diameter is between 30 to 120 micrometers.

In still yet another embodiment of the invention, the distance between the pores is about 3 times the diameter of the pore.

In still yet another embodiment of the invention, the stent has a filter in which the filter membrane is comprised of a fine mesh material that has a pore size capable of blocking emboli while allowing continued blood flow.

In still yet another embodiment of the invention, the stent is a stent graft or intraluminal graft.

In still yet another embodiment the invention is directed to a method of forming a stent. In one such embodiment, a molten piece of bulk-solidifying amorphous alloy is cast into near-to-net shape for a stent component or as a precursor to a stent component. In another preferred embodiment of the invention, a feedstock of bulk-solidifying amorphous alloy is heated to around the glass transition temperature and formed into a near-to-net shape component for a stent or as a precursor to a stent component.

In still yet another embodiment of the invention, the surface of the stent is modified by chemical treatment. In such an embodiment, the chemical treatment may use a mixed aqueous solution of hydrofluoric acid or nitric acid or sodium hydroxide, or a thermal treatment under in-air oxidation, or a combination of the aforementioned treatments.

In still yet another embodiment, the invention is directed to a method of duplicating desired morphological features onto the surface of the stent.

In still yet another embodiment of the invention, the fabrication process compromises creating a pattern of slots or apertures in a flexible metallic tubular member, by processes including but not limited to, electrostatic discharge machining (EDM), chemical milling, ablation and laser cutting. These slots or apertures may be cut completely or partially through the wall of the flexible metallic tubular member.

In still yet another embodiment of the invention, the fabrication process compromises a finishing process which includes electro-polishing or chemical etching to provide a highly polished and smoothed surface.

In still yet another embodiment of the invention, the stent strut design provides for a specific amount of elastic deformation.

In still yet another embodiment of the invention, the stent strut design is such that some strut segments are elastically deformed when collapsing the stent to a compact size and other strut segments remain undeformed.

In still yet another embodiment of the invention, specific stent strut design permits certain segments to be elastically deformed more than other stent strut segments.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
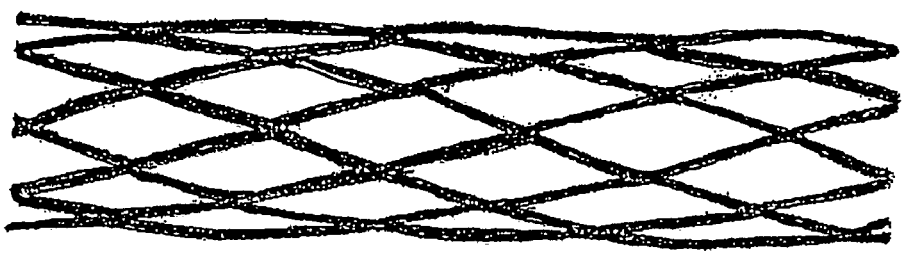
FIG. 1 shows a schematic of one embodiment of a stent design according to the current invention.

The current invention is directed to stents made of bulk-solidifying amorphous alloys. Stents, in their expanded form, are generally designed to sustain substantial flexural strain in the longitudinal direction, and ability to carry load in radial direction. Even though, sophisticated designs are utilized to improve such desired characteristics of the stents, the metals and alloys currently used to manufacture the stents show major shortcomings, especially for the stents of smaller diameter.

Applicants have discovered that bulk-solidifying amorphous alloys have general characteristics, which can be tailored to be particularly useful in stent applications. These characteristics, as will be shown below, make bulk-solidifying amorphous alloys uniquely suited as a new class of materials for use in stents.

Bulk solidifying amorphous alloys are a recently discovered family of amorphous alloys, which can be cooled at substantially lower cooling rates, of about 500 K/sec or less, and substantially retain their amorphous atomic structure. As such, these materials can be produced in thickness of 1.0 mm or more, substantially thicker than conventional amorphous alloys of typically 0.020 mm which require cooling rates of $10^5$ K/sec or more. Furthermore, these alloys are capable of showing glass transition and form an extended super-cooled liquid regime before the onset of the crystallization. For example, these alloys have typically a $\Delta T$ (temperature range between the glass transition and the onset of crystallization)

of 50° C. or more and up to 100° or more for specific compositions. As such they can be deformed to significant extent with ease under very small stress. Furthermore, bulk-solifying amorphous alloys have high yield strength and good corrosion resistance. Exemplary alloy materials are described in U.S. Pat. Nos. 5,288,344; 5,368,659; 5,618,359; and 5,735,975 (the disclosures of which are incorporated in their entirety herein by reference).

One exemplary family of bulk solidifying amorphous alloys can be described as $(Zr,Ti)_a(Ni,Cu, Fe)_b(Be,Al,Si,B)_c$, where a is in the range of from 30 to 75, b is in the range of from 5 to 60, and c in the range of from 0 to 50 in atomic percentages. Furthermore, those alloys can accommodate substantial amounts of other transition metals up to 20% atomic, and more preferably metals such as Nb, Cr, V, Co, Ta, Mo, W. A preferable alloy family is $(Zr,Ti)_a(Ni,Cu)_b(Be)_c$, where a is in the range of from 40 to 75, b is in the range of from 5 to 50, and c in the range of from 5 to 50 in atomic percentages. Still, a more preferable composition is $(Zr,Ti)_a(Ni,Cu)_b(Be)_c$, where a is in the range of from 45 to 65, b is in the range of from 7.5 to 35, and c in the range of from 10 to 37.5 in atomic percentages. Another preferable alloy family is $(Zr)_a(Nb,Ti)_b(Ni,Cu)_c(Al)_d$, where a is in the range of from 45 to 65, b is in the range of from 0 to 10, c is in the range of from 20 to 40 and d in the range of from 7.5 to 15 in atomic percentages. These bulk-solidifying amorphous alloys can sustain strains up to 1.5% or more and generally around 1.8% without any permanent deformation or breakage. The yield strength of bulk solidifying alloys range from 1.6 GPa and reach up to 2.5 GPa and more exceeding the current state of the Titanium alloys.

Another set of bulk-solidifying amorphous alloys are ferrous metals (Fe, Ni, Co) based compositions. Examples of such compositions are disclosed in U.S. Pat. No. 6,325,868; (A. Inoue et. al., Appl. Phys. Lett., Volume 71, p 464 (1997); (Shen et. al., Mater. Trans., JIM, Volume 42, p 2136 (2001)); and Japanese patent application 2000126277 (Publ. #0.2001303218 A), all of which are incorporated herein by reference. One exemplary composition of such alloys is $Fe_{72}Al_5Ga_2P_{11}C_6B_4$. Another exemplary composition of such alloys is $Fe_{72}Al_7Zr_{10}Mo_5W_2B_{15}$. Although, these alloy compositions are not processable to the degree of the above-cited Zr-base alloy systems, they can still be processed in thicknesses around 1.0 mm or more, sufficient enough to be utilized in the current invention. Similarly, these materials have elastic strain limits higher than 1.2% and generally around 1.8%. The yield strength of these ferrous-based bulk-solidifying amorphous alloys is also higher than the Zr-based alloys, ranging from 2.5 GPa to 4 GPa, or more.

In general, crystalline precipitates in bulk amorphous alloys are highly detrimental to the properties of bulk-solidifying amorphous alloys, especially to the toughness and strength of these materials, and, as such, such precipitates are generally kept to as small a volume fraction as possible. However, there are cases in which, ductile crystalline phases precipitate in-situ during the processing of bulk amorphous alloys, are indeed beneficial to the properties of bulk amorphous alloys, and especially to the toughness and ductility of the materials. Such bulk amorphous alloys comprising such beneficial precipitates are also included in the current invention. An exemplary composition of such alloy is $Zr_{56.2}Ti_{13.8}Nb_{5.0}Cu_{6.9}Ni_{5.6}Be_{12.5}$ in atomic percentages. This alloy has a low elastic modulus of from 70 GPa to 80 GPa depending on the specific microstructure of ductile-crystalline precipitates. Further, the elastic strain limit is 1.8% or more and the yield strength is 1.4 GPa and more.

Although a number of bulk solidifying amorphous alloy compositions are described above, the alloy can also be preferably selected to be free of Ni or Al or Be in order to address high sensitivity or allergy of specific population groups to such metals.

The unique advantage of utilizing bulk solidifying amorphous alloys is not a single specific property, but rather the simultaneous existence of a set of properties. Furthermore, these properties can be obtained in various design packages with a high degree of fabricability, especially for the components of small dimensions as found in stents. As such, these alloys show their advantage best in smaller stent dimensions such as for the stents of 6.0 mm or less in diameter, and especially for the stents of under 3.0 mm in diameter.

First of all, bulk-solidifying amorphous alloys have typically 50% or much more higher yield strength than conventional alloys of its constituent elements. For example, a titanium base crystalline alloy (such as Ti-6-4) has a yield strength typically around 850 MPa, whereas Ti-base amorphous alloys have a yield strength around 1900 Mpa and higher. Secondly, bulk solidifying amorphous alloys have a very high elastic strain limit, which characterizes a material's ability to sustain strains without permanent deformation. Typically bulk-solidifying amorphous alloys have elastic strain limits of around 1.8% or higher. The combination of very high yield strength and very high elastic strain limit provides a unique advantage of designing stents with high load carrying ability in radial directions and meanwhile sustain very high flexural strains in longitudinal directions.

In a typical stent application in the body, stents are inserted in a very compact package to facilitate the aiding of insertion and movement to the desired position in the vessel. Then, the stent is expanded into its operational shape in two distinct methods. In the first method, generally used for stainless steel or pure titanium, the stent is plastically deformed into its operational shape by means of an angioplasty balloon. In the other method, generally reserved for shape-memory alloys such as Nitinol, the stent expands by the aid of self "memory energy" put into the stent package utilizing the shape memory effect of specific phase transformation property for these alloys. The latter stents are called self-expanding and preferred due to such ability, which eliminates the need for operation of a separate angioplasty balloon to expand the stent.

Figure 2:
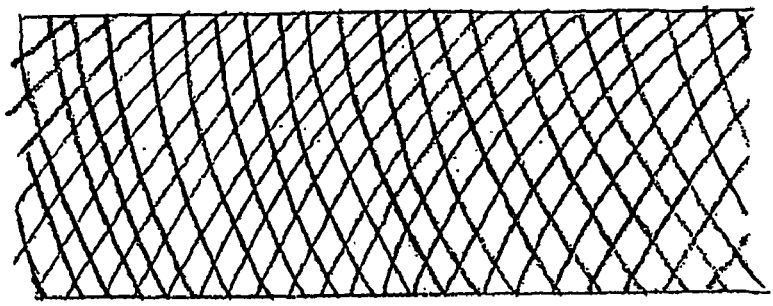
FIG. 2 shows a schematic of a second embodiment of a stent design according to the current invention.
Figure 3:
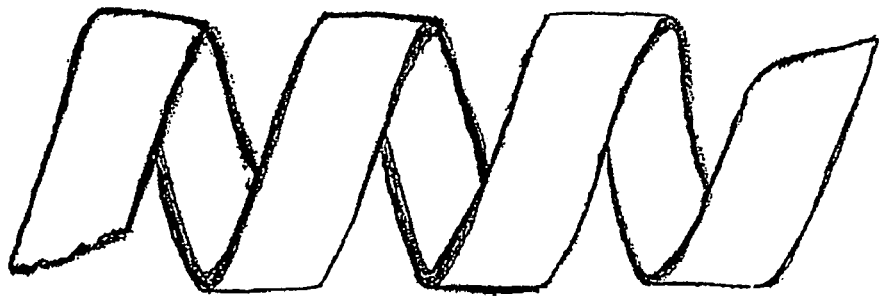
FIG. 3 shows a schematic of a third embodiment of a stent design according to the current invention.
Figure 4:
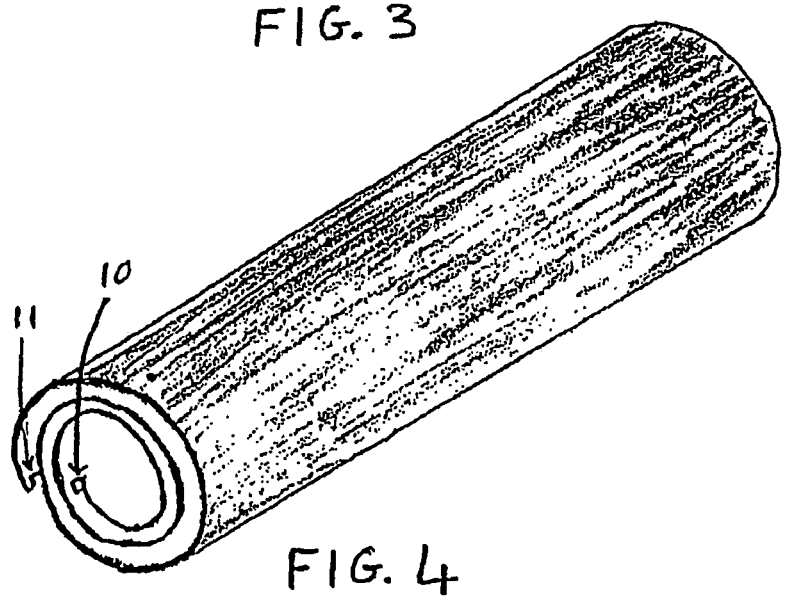
FIG. 4 shows a schematic of a fourth embodiment of a stent design according to the current invention.

In either case, the yield strength of stent material is generally under 1 GPa. Accordingly, the stents are made with larger wall-thickness to provide resistance and load carrying ability in radial directions so that restenosis forces from the vessel can be counteracted. However, this is not desirable, as the stent will have a high form factor (the form factor is defined for the radial direction as the ratio of the area of open space (scaffolded area) to the area covered by stent wall thickness). Generally, for stent diameters of 3.0 mm or less, this becomes a more critical issue that, where the form factor of stent becomes unacceptable for practice when conventional stent metals and alloys are used. Even though, there exists some metals and alloys with very high yield strengths exceeding 1 GPa, (such as maraging steel), these alloys are not deemed useful due to fabricability issues in complex and small geometries, as well as corrosion and bio-compatibility issues. Furthermore, such alloys provide major problems in packaging stents into compact shapes for delivery since they do not have shape-memory The use of bulk-solidifying amorphous alloys allows the production of stents with a smaller form factor (utilizing the higher yield strength of bulk-solidifying amorphous alloys), and a packaging method utilizing the truly mechanical elastic behavior of the material. For example, the higher yield strength of bulk-solidifying amorphous alloys can be utilized to make stents with smaller wall thicknesses, while maintaining an acceptable radial structural integrity. Meanwhile, this smaller wall thickness can be beneficially utilized, in turn, to facilitate a stent structure that is more flexible in a longitudinal direction. Furthermore, the smaller wall thickness greatly facilitates the packaging of stents into a compact geometry, as such, various prior art stent designs can be more effectively utilized. For example, FIG. 1 to 4 show a variety of exemplary conventional stent designs that might be formed using a bulk-solidifying amorphous alloy according to the present invention including: mesh designs, as shown in FIGS. 1 and 2, and non-mesh designs, such as helical coils and rolls as shown in FIGS. 3 and 4.

Moreover, new novel stent designs can be developed to readdress old applications and to newly address new stent applications and designs. For example, FIG. 4 shows a collapsed stent with locking mechanisms 10 and 11, which when expanded interlock to maintain the desired shape of stent. In addition, to more complicated stent designs, these properties, along with the added benefit of various fabrication methods unique to bulk-solidifying amorphous alloys, makes the development of stents with diameter of under 3.0 mm more feasible.

Accordingly, in one embodiment of the current invention a stent is fabricated from a bulk solidifying amorphous alloy with a yield strength of at least 1.5 GPa or more, preferably with a yield strength of 2.0 GPa or more, and most preferably with a yield strength of 3.0 GPa or more. Additionally, the bulk solidifying amorphous alloy is selected such that the elastic strain limit is 1.5% or higher and more preferably 1.8% or higher. In the delivery package, the stent is compacted (or compressed) by mechanical forces such that the bulk solidifying amorphous alloys is strained up to 1.0% or higher, and preferably 1.5% or higher, but not exceeding its elastic strain limit. (Herein, the strain is intended for the stent material and not the strain of the overall geometry). Subsequent to the stent insertion, the retaining mechanical forces are released and the stent self-expands to reduce the strain below 0.5% and preferably below 0.25%, meanwhile exerting an outward scaffolding pressure to the vessel.

Although a number of potential bulk-solidifying amorphous alloys are discussed above, Zr/Ti base bulk-solidifying amorphous are preferred due to their excellent paramagnetic characteristics (lack of ferromagnetism) and better bio-compatibility. Paramagnetic characteristics are desired for MRI (magnetic-resonance imaging) compatibility. Zr-base bulk-solidifying amorphous alloys are further preferred as they generally have more robust processability characteristics, which allows a better ability to form these materials into the necessary sophisticated designs.

Ferrous-base bulk-solidifying amorphous alloys may also be used and are preferred for their relatively higher yield strength of 3.0 GPa or more. Ferrous alloys are preferably selected such that they have enough alloying non-magnetic alloying elements to retard the ferro-magnetic properties of Fe and Ni to provide MRI compatibility. One such preferred element for retarding ferro-magnetism in ferrous alloys is Manganese. Another preferred element is Copper. Zr and Ti can also be utilized effectively as alloying additions to retard ferro-magentism in such ferrous base alloys, provided sufficient leeway is given to preserve the ability of bulk-solidification of the final alloy into an amorphous structure.

Another important characteristic, which can be tailored with using bulk solidifying amorphous alloys, is radio-opacity. This is highly desirable during the application or placement of a stent in order to locate stent location and length more precisely using fluorescence imaging. Zr-base bulk-solidifying amorphous alloys are preferred for better radio-opacity than Ti-base alloys. Further, elements of high atomic numbers, such as Ta, Hf, W can be quite readily added as alloying additions into Zr—Ti base alloys for improved radio-opacity. Furthermore, these elements (Hf, Ta, W) of high atomic number can further be used as partial replacements for lower atomic number elements such as Zr, Nb, and Mo, respectively, to provide better radio-opacity. Pd can also be used as a replacement for Ni or Co to improve radio-opacity. Due to the unique atomic structure, such alloying additions and/or replacements can be more readily used in bulk solidifying amorphous alloys, without sacrificing other beneficial properties mentioned above, unlike conventional metals and alloys.

It is also possible to form micro-structured surface morphologies by design using bulk-solidifying amorphous alloys. Such microstructures can be in the shape of pores, which, for example, aid drug coating and carrying. Herein, the pores are differentiated from slots and apertures and are rather defined as surface depressions and do not necessarily pass all the way through the wall thickness of the stent. The unique amorphous atomic microstructure of these materials responds uniformly to the forming operations of micron and sub-micron scales making it possible to form features within the desirable morphological ranges. This is in distinct contrast to conventional metals and alloys, where the microstructure of the material is characterized by crystallites (individual grains typically with dimensions of few to several hundreds microns), each of which has different crystallographic orientation and, as such, responds non-uniformly to shaping and forming operations.

Figure 5:
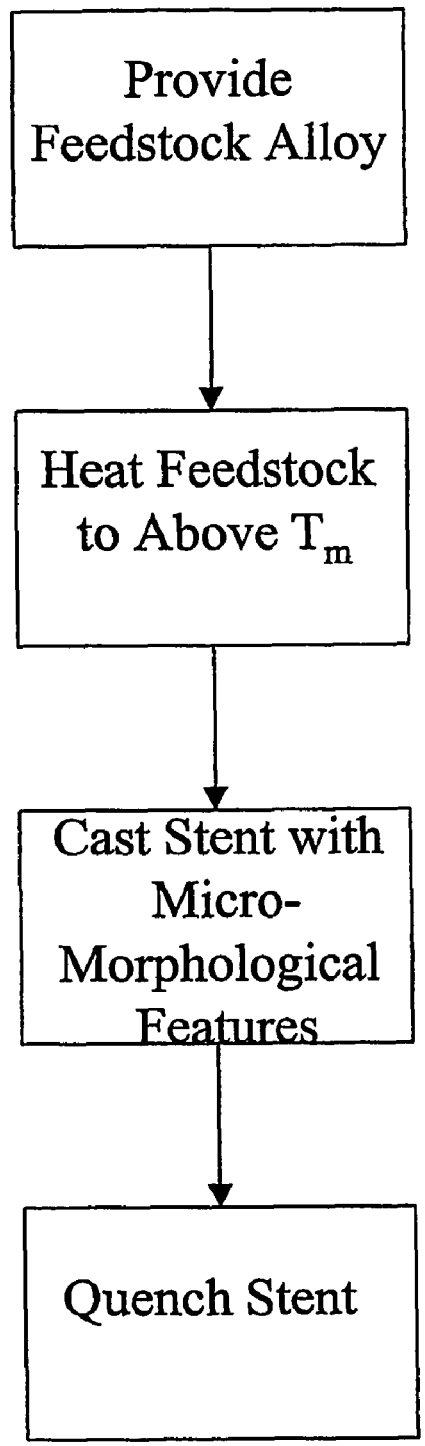
FIG. 5 shows a flow chart of one exemplary embodiment of a method of forming stents in accordance with the current invention.

The micro-structured surface morphology according to the current invention can be produced in two alternative ways. In a first exemplary method, as outlined in FIG. 5, the surface morphology can be simultaneously formed during the fabrication of stent components by casting methods. In such an embodiment the mold surfaces used in the casting operation can be pre-configured to have the negative impression of the desired surface microstructure so that the bulk-solidifying amorphous alloy replicates such features upon casting. The relatively low melting temperature of bulk-solidifying amorphous alloys and the lack of any first-order phase transformation during the solidification readily enables the replication of micron sized mold features during the casting of the stent components. Such a process is highly desirable as several steps of post-finishing and surface preparation operations can be reduced or eliminated.

Figure 6:
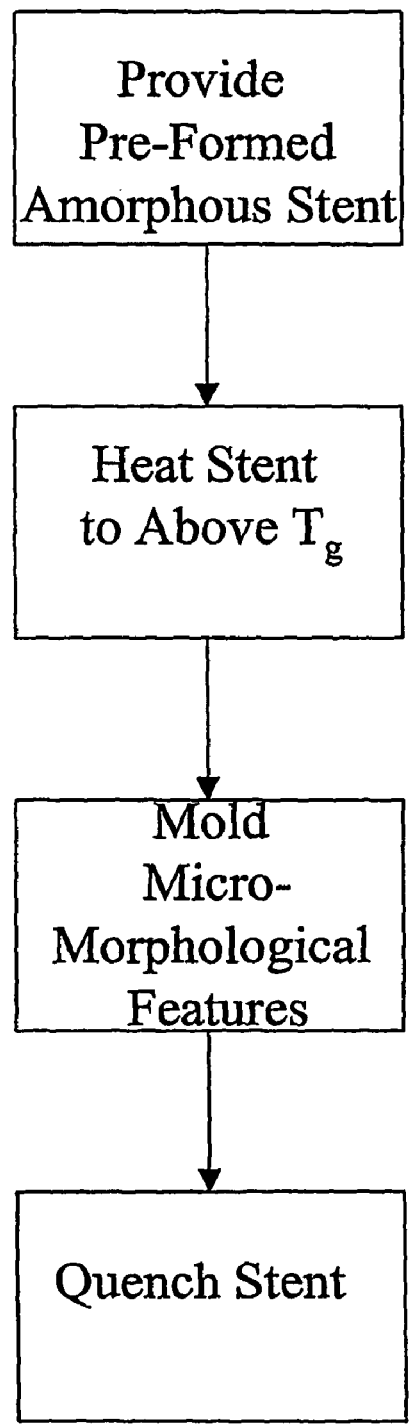
FIG. 6 shows a flow chart of another exemplary embodiment of a method of forming stents in accordance with the current invention.

In an alternative exemplary method, as outlined in FIG. 6, a pre-fabricated stent component made of bulk-solidifying amorphous alloy is subjected to a surface micro-structuring process at around the glass transition temperature of the bulk-solidifying amorphous alloy material. In such an embodiment, the fabricated stent component is heated to around the glass transition temperature and pressed against a mold having the negative impression of the desired surface microstructure. As the bulk solidifying amorphous alloy will readily transition into a viscous liquid regime upon heating, the replication of the desired surface morphology can readily take place. In this embodiment of the method, bulk-solidifying amorphous alloys with a large $\Delta Tsc$ (supercooled liquid region) is preferred. Bulk-solidifying amorphous alloys with a $\Delta Tsc$ of more than 60° C., and still more preferably a $\Delta Tsc$ of 90° C. and more are desired for a high-definition surface micro-structuring. One exemplary of such alloy having $\Delta Tsc$ of more than 90° C. is $Zr_{47}Ti_8Ni_{10}Cu_{7.5}Be_{27.5}$. ($\Delta Tsc$ is defined as the difference between Tx (the onset temperature of crystallization) and Tsc (the onset temperature of supercooled liquid region). These values can be conveniently determined by using standard calorimetric techniques such as by DSC measurements at 20° C./min).

Once a suitable stent component is fabricated into a near-net shape, further fabrication processes such as electrostatic discharge machining (EDM), chemical milling, ablation, and laser cutting can be utilized to cut slots or apertures completely or partially through the wall of the flexible metallic tubular member. Such processes, when properly applied, will not have any significant effect on the above mentioned beneficial mechanical properties. Furthermore, final-finishing operations such as electro-polishing or chemical etching as well as anodizing can be applied to provide a highly polished and smoothed surface. Such processes have added advantage in the bulk solidifying amorphous alloys that, the uniformity of the microstructure to the atomic level will facilitate the effective use of such operations without any such deficiencies which are found in crystalline alloys due to crystalline directions and preferential etching.

Finally, various casting processes, such as metal mold casting and investment casting can be utilized to fabricate stent components of bulk-solidifying amorphous alloys employing sufficiently fast cooling rates. Small form-factor tubular stent members can be readily produced with very high yield strengths of 1.5 Gpa and higher. Furthermore, utilizing processes such as investment casting, highly intricate and customized stent components can be cast. Such as-cast components will have a very high yield strength exceeding 1.5 Gpa and an exceptionally high elastic strain limit of 1.5% or higher without any subsequent thermo-mechanical processes or heat treatment.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

What is claimed is:

1. A stent of a radially compactable generally tubular body comprising a bulk-solidifying amorphous alloy, wherein the alloy is subjected to an elastic strain of at least 1.0% in a compacted form of the stent.

2. The stent described in claim 1, wherein the amorphous alloy has an elastic strain of at least 1.5%.

3. The stent described in claim 1, wherein the amorphous alloy has an elastic strain of at least 1.5%, and a yield strength of more than 1.4 Gpa.

4. The stent described in claim 1, wherein the amorphous alloy has an elastic strain of at least 1.8%, and a yield strength of more than 1.9 Gpa.

5. The stent described in claim 1, wherein the amorphous alloy is subjected to an elastic strain of at least 1.5% in a compacted form of the stent.

6. The stent described in claim 1, wherein the amorphous alloy is subjected to an elastic strain of at least 1.8% in a compacted form of the stent.

7. The stent described in claim 1, wherein the amorphous alloy is subjected to an elastic strain of less than 0.5% in an expanded form of the stent.

8. The stent described in claim 1, wherein the amorphous alloy has a delta T of greater than 90° C.

9. The stent described in claim 1, wherein the amorphous alloy is a Zr/Ti base bulk-solidifying amorphous alloy.

10. The stent described in claim 1, wherein the stent has a cross-section selected from the group consisting of hexagonal and round.

11. The stent described in claim 1, wherein the body comprises a plurality of pieces arranged in a conformation selected from the group consisting of coiled spring, helical wound spring coil, zigzag pattern, diamond shaped, and non-mesh designs.

12. The stent described in claim 1, wherein the wall of the body has a plurality of aperture openings.

13. The stent described in claim 1, wherein the body covers between 9 and 20% of a vessel into which the stent is implanted.

14. The stent described in claim 1, wherein the body covers at least 80% of a vessel into which the stent is implanted.

15. The stent described in claim 1, wherein the body comprises at least two tubular segments which overlap or abut to form a single tubular body.

16. The stent described in claim 1, wherein the stent is self-expanding.

17. The stent described in claim 1, wherein the body is branched.

18. The stent described in claim 1, wherein the body has a wall thickness of less than 0.5 mm.

19. The stent described in claim 1, wherein the body has a wall thickness of less than 0.25 mm.

20. The stent described in claim 1, wherein the stent is one of either a stent graft or intraluminal graft.

21. A method of forming a stent, comprising:
   providing a molten piece of bulk-solidifying amorphous alloy;
   providing a mold in the shape of a desired stent component;
   casting the molten amorphous alloy into a plurality of near-to-net shape stent components;
   assembling a stent from the stent components; and
   compacting the stent radially to form a compacted stent, wherein the amorphous alloy piece is subjected to an elastic strain of at least 1.0% during compacting.

22. The method as described in claim 21, further comprising finishing an outer surface the stent, wherein the finishing is selected from a process selected from the group consisting of electro-polishing and chemical etching.

23. The method as described in claim 21, further comprising modifying an outer surface of the stent by a treatment selected from the group consisting of chemical treatment, thermal treatment, and a combination thereof.

24. A method of forming a stent, comprising:
   providing a feedstock a bulk-solidifying amorphous alloy;
   heating the feedstock to around the glass transition temperature of the amorphous alloy;
   providing a mold in the shape of a desired stent component;
   molding the molten amorphous alloy into a plurality of near-to-net shape stent components;
   assembling a stent from the stent components; and
   compacting the stent radially to form a compacted stent, wherein the amorphous alloy piece is subjected to an elastic strain of at least 1.0% during compacting.

25. The method as described in claim 24, further comprising finishing an outer surface the stent, wherein the finishing is selected from a process selected from the group consisting of electro-polishing and chemical etching.

26. The method as described in claim 24, further comprising modifying an outer surface of the stent by a treatment selected from the group consisting of chemical treatment, thermal treatment, and a combination thereof.

27. A method of forming a stent comprising:
providing a tubular body made of a bulk-solidifying amorphous alloy;
processing the tubular body to form a pattern of surface features therein, wherein the surface features extend at least partially through the wall of the body; and
compacting the stent radially to form a compacted stent, wherein the amorphous alloy is subjected to an elastic strain of at least 1.0% during compacting.

28. The method as described in claim 27, wherein the processing includes a manufacturing method selected from the group consisting of electrostatic discharge machining (EDM), chemical milling, ablation and laser cutting.

29. The method as described in claim 27, further comprising finishing an outer surface the stent, wherein the finishing is selected from a process selected from the group consisting of electro-polishing and chemical etching.

30. The method as described in claim 27, further comprising modifying an outer surface of the stent by a treatment selected from the group consisting of chemical treatment, thermal treatment, and a combination thereof.

* * * * *